US00PP26274P3

(12) United States Plant Patent
Giumarra et al.

(10) Patent No.: US PP26,274 P3
(45) Date of Patent: Dec. 29, 2015

(54) GRAPE PLANT NAMED 'ARRATHIRTY'

(50) Latin Name: *Vitis vinifera*
Varietal Denomination: ARRATHIRTY

(71) Applicant: AGRICULTURAL RESEARCH AND DEVELOPMENT LIMITED LIABILITY COMPANY, Bakersfield, CA (US)

(72) Inventors: Sal Giumarra, Bakersfield, CA (US); Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 131 days.

(21) Appl. No.: 13/999,792

(22) Filed: Mar. 21, 2014

(65) Prior Publication Data

US 2015/0271974 P1 Sep. 24, 2015

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Christie, Parker & Hale, LLP

(57) ABSTRACT

A new distinct variety of grapevine named 'ARRATHIRTY' abundantly forms attractive small-to-medium firm and meaty seedless berries with a yellow/green skin coloration; in medium-to-large clusters which display a sweet natural flavor. The fruit commonly is ready for harvesting during June in San Joaquin Valley of Central California, U.S.A, and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRATHIRTY'.

BACKGROUND OF THE INVENTION

A breeding program was initiated during the late 90's near Bakersfield in San Joaquin Valley of Central California. In 2008, during this breeding program, a new variety of *Vitis vinifera* was created by deliberate cross breeding of two parent plants by emasculation of the pollen bearing organ of the female and introducing pollen from another male origin. The female parent of the new variety was C.R. which is a medium-sized red seedless grape variety with a crisp texture and a natural flavor (non-patented in the United States). The male parent (i.e. the pollen parent) of the new variety was GRAPES which is an oval shaped, creamy green colored, seedless variety with a Muscat flavor (patented in the United States).

Comparison of 'ARRATHIRTY' with its parents:

| | ARRATHIRTY | C.R. (Mother) | GRAPAES (Father) | Thompson Seedless (Comparison Variety) |
|---|---|---|---|---|
| Seed trace | None | None | Small | Small to none |
| Berry shape | Elongated | Elliptic | Narrow Ellipsoid | Oblong |
| Bunches per vine | 48 | 28-32 | 32-36 | 30 |
| Fertility | High | Medium | Very high | Low |

The parentage of the new variety can be summarized as follows:

C.R.xGRAPAES

An artificial pollination was created, and the result was an embryo which possessed unique genetic qualities. The rudiments resulting from the above pollination were embryo rescued.

In 2009 the plant was transplanted to Bakersfield in San Joaquin Valley of Central California.

It was found that the new grapevine of the present invention possesses the following combination of characteristics:

(a) Forms attractive small-to-medium firm & meaty seedless berries with a yellow-green skin coloration; in medium-to-large clusters which display a sweet natural flavor, (b) Commonly bears fruit during the month of June in the San Joaquin Valley of Central California, U.S.A., and (c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2011 near Bakersfield in the San Joaquin Valley of Central California, U.S.A. by grafting on mature Thompson rootstock (non-patented in the United States). Such asexual propagation has been conducted thereafter in successive years through 2012, and has shown that the characteristics of the new variety are strictly transmissible from one generation to another. Accordingly, the new variety undergoes asexual propagation in a true to type manner.

SUMMARY OF THE INVENTION

The new variety 'ARRATHIRTY' is a medium size, yellow-green seedless table grape with a very high production, e.g., about 48 bunches per vine, and an average of about one to two bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical specimens of vegetative growth of six year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATHIRTY'.

DETAILED BOTANICAL DESCRIPTION

The chart used in the identification of colors is The R.H.S. Colour Chart of The ROYAL HORTICULTURAL SOCIETY 1995 edition. The description is based on the observation of plants growing on 'Thompson Seedless' rootstock outdoors near San Joaquin Valley of Central California, U.S.A.

Vine:
- *Vigor*.—Vigorous upright shoots.
- *Productive capacity*.—Bearing at a natural, average capacity. Spur pruning.
- *Trunk*.—Strong and developed. Ranges from 2"-2"⅜". Rough with a fibrous, shaggy exterior. Light maple brown coloring.

Time of bud burst: Early. Feb. 15, 2013 in Bakersfield, Calif.

Young shoot:
- *Openness of tip*.—Half open.
- *Prostrate hairs on tip*.—Medium.
- *Anthocyanin coloration of prostate hairs on tip*.—Medium.
- *Erect hairs on tip*.—Medium.

Young leaf:
- *Color of upper side of blade*.—Yellow-green (146-B).
- *Prostrate hairs between main veins on lower side of blade*.—Medium.
- *Erect hairs on main veins on lower side of blade*.—Medium.

Shoot:
- *Attitude* (*before tying*).—Horizontal.
- *Color of dorsal side of internodes*.—Green and red (yellow green 144-B and greyed orange 178-B).
- *Color of ventral side of internodes*.—Green and red (yellow green 144-B and greyed orange 178-B).
- *Color of dorsal side of nodes*.—Green and red (yellow green 144-B and greyed orange 178-B).
- *Color of ventral side of nodes*.—Green and red (yellow green 144-B and greyed orange 178-B).
- *Erect hairs on internode*.—Sparse.
- *Number of tendrils*.—6 at bloom.
- *Length of tendrils*.—Long (9").
- *Color of tendrils*.—Yellow green 144-C.

Flower:
- *Sexual organs*.—Fully developed stamens and fully developed gynoecium.

Mature leaf:
- *Size of blade*.—7"×6".
- *Shape of blade*.—Wedge-shaped.
- *Blistering of upper side of blade*.—Medium.
- *Number of lobes*.—Seven.
- *Depth of upper lateral sinuses*.—Deep.
- *Arrangement of lobes of upper lateral sinuses*(*only varieties with lobed leaves*).—Slightly overlapped.
- *Arrangement of lobes petiole sinus*.—Wide open.
- *Length of teeth*.—Long.
- *Ratio length/width of teeth*.—Medium.
- *Shape of teeth*.—Both sides straight.
- *Proportion of main veins on upper side of blade with anthocyanin coloration*.—Medium.
- *Prostrate hairs between main veins on lower side of blade*.—Medium.
- *Erect hairs on main veins on lower side of blade*.—Medium.
- *Length of petiole compared to length of middle vein*.—Equal.
- *Top side color*.—Green (137-A).
- *Bottom side color*.—Green (138-B).
- *Texture*.—Rough.
- *Vein color*.—Green (138-B) and greyed orange (178-B).
- *Petiole length*.—7".
- *Petiole color*.—Green (138-B) and greyed red 178-B).

Reporductive organs:
- *Color*.—Green (137-B).
- *Size*.—0.003305".

Time of beginning of ripening: Very early. Jun. 29, 2013 in Bakersfield, Calif.

Bunch:
- *Size* (*penduncle excluded*).—Very large.
- *Density*.—Lax.
- *Length of penduncle primary bunch*.—Medium.
- *Average bunch weight*.—2 lbs.

Berry:
- *Size*.—Medium.
- *Length*.—1.25".
- *Shape*.—Obtuse ovoid.
- *Diameter*.—1".
- *Weight*.—0.35 oz.
- *Color of skin* (*without bloom*).—Green (149-C).
- *Ease of detachment from pedicle*.—Difficult.
- *Thickness of skin*.—Thin.
- *Anthocyanin coloration of flesh*.—Absent or very weak.
- *Firmness of flesh*.—Very firm.
- *Particular flavor*.—None.
- *Formation of seeds*.—None.
- *Market use of observed plant*.—Fresh market.
- *Berries per bunch*.—90-120.

Woody shoot:
- *Main color*.—Yellowish brown (greyed orange 165-D).

Age and growing conditions: Six years growing under Y system in South Joaquin Valley (hot, dry summers).

Shipping characteristics: (E.g. number of days fruit has been stored under specific conditions): Fruit was in cold storage. Stored in poly bags inside Styrofoam boxes with sulphur pads.

*After* 60 *days*.—Rachises were 60% green; 5% berry shuttering; no berry wrinkling or cracks were apparent.

DNA PROFILE

To further the characterize the new Arra variety DNA was extracted from dried leaf samples and DNA profiles were obtained at California Seed & Plant Lab, California USA using base pairs for 10 standard microsatellite DNA markers. The data is presented hereafter.

| Micro-satellite DNA Marker | Allele Sizes in Base Pairs | |
|---|---|---|
| M 1 | 236 | 238 |
| M 2 | 247 | 249 |
| M 3 | 185 | 194 |
| M 4 | 210 | 214 |
| M 5 | 273 | 273 |

-continued

| Micro-satellite DNA Marker | Allele Sizes in Base Pairs | |
|---|---|---|
| M 6 | 133 | 151 |
| M 7 | 189 | 193 |
| M 8 | 251 | 257 |
| M 9 | 212 | 214 |
| M 10 | 237 | 249 |

The 'ARRATHIRTY' variety has not been observed under all possible environmental conditions to date. Accordingly, it is possible that the phenotypic expression may vary somewhat with changes in light intensity and duration, cultural practices, and other environmental conditions.

What is claimed is:

1. A new and distinct variety of grapevine, botanically known as *Vitis vinifera*, identified as 'ARRATHIRTY', substantially as shown and described herein.

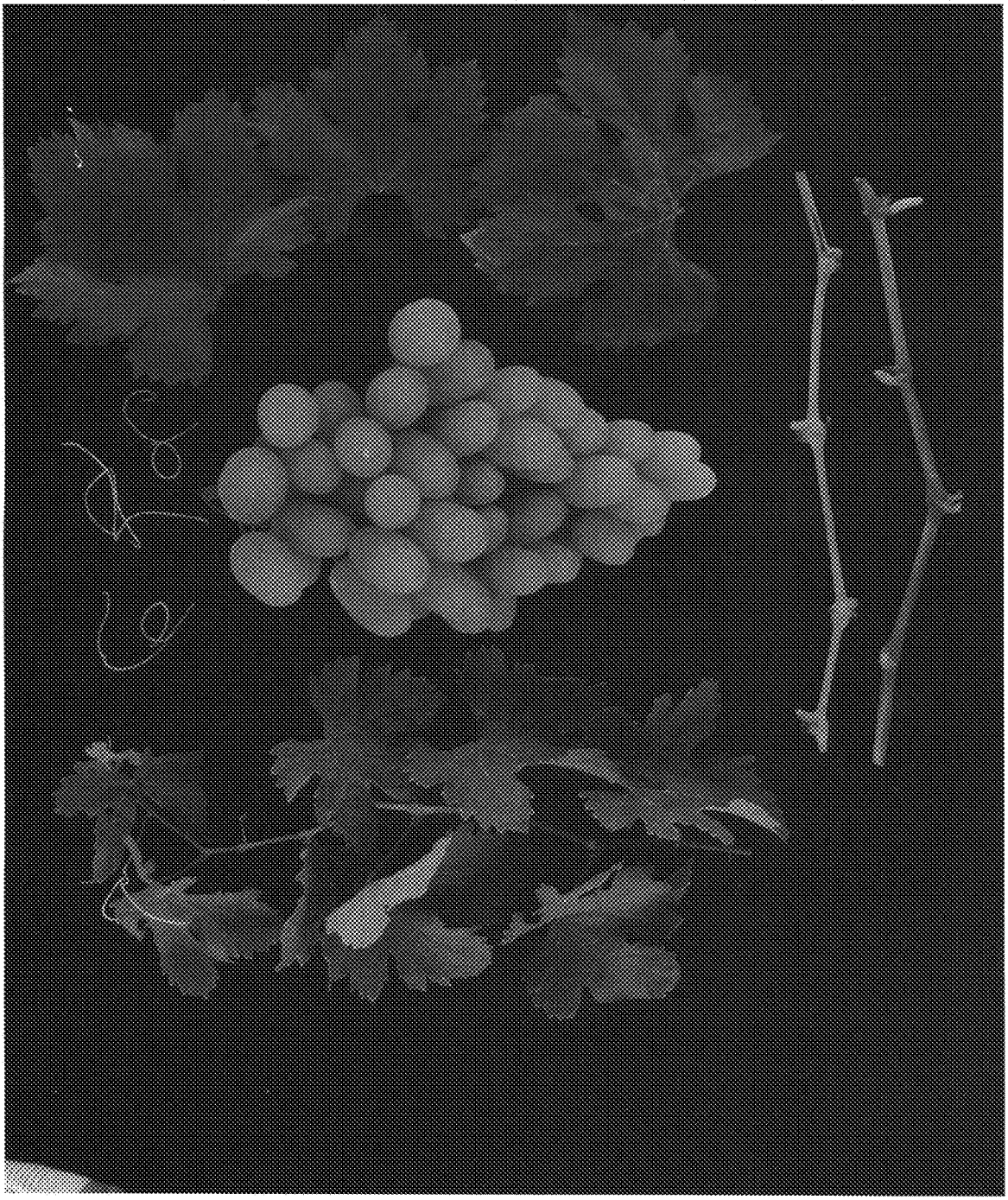

* * * * *